United States Patent [19]

Helms

[11] Patent Number: 5,054,123
[45] Date of Patent: Oct. 8, 1991

[54] PROGRAM SUN VISOR

[76] Inventor: James F. Helms, 511 Fall River, Houston, Tex. 77024

[21] Appl. No.: 533,525

[22] Filed: Jun. 5, 1990

[51] Int. Cl.⁵ ............................................. A61F 9/00
[52] U.S. Cl. .......................................... 2/12; 2/200; 2/209.1
[58] Field of Search ..................... 2/12, 15, 171, 171.1, 2/171.2, 174, 184.5, 209.1, 209.3, 209.7, 177

[56] References Cited

U.S. PATENT DOCUMENTS

| | | | |
|---|---|---|---|
| D. 196,166 | 9/1963 | Ellis | D2/247 |
| D. 267,364 | 12/1982 | DeLozada | D2/247 |
| D. 282,405 | 2/1986 | DeLozada | D2/247 |
| 1,030,173 | 6/1912 | Haggerty | 2/12 |
| 1,631,210 | 5/1926 | Johnson | 2/12 |
| 2,009,855 | 6/1935 | Osmer | 2/12 |
| 2,081,088 | 5/1937 | Guntrup | 2/12 |
| 2,521,017 | 9/1950 | Moen et al. | 2/200 |
| 2,679,047 | 5/1954 | Bozzi | 2/12 |
| 2,682,668 | 7/1954 | Hoeflich | 2/200 |
| 3,184,757 | 5/1965 | Pennington | 2/12 |
| 3,266,056 | 9/1960 | Villers et al. | D2/247 |
| 3,271,778 | 5/1961 | Ferguson | D2/247 |
| 4,232,403 | 11/1980 | Burtis | 2/209.1 |
| 4,246,659 | 1/1981 | Lyons | 2/200 |
| 4,247,957 | 2/1981 | Rogers | 2/12 |
| 4,335,471 | 6/1982 | Quigley, Jr. et al. | 2/200 |
| 4,386,126 | 5/1983 | Turner | 2/12 |
| 4,670,910 | 6/1987 | Rosasco | 2/12 |
| 4,747,164 | 5/1988 | Foulke | 2/171 |
| 4,837,865 | 6/1989 | Roth | 2/209.1 |

*Primary Examiner*—Werner H. Schroeder
*Assistant Examiner*—Diana L. Biefeld
*Attorney, Agent, or Firm*—Sue Z. Shaper

[57] ABSTRACT

A one-time trouble-free sun visor made from a detachable page of a program, the page having a perforated line that separates a substantially rectangular interior portion of the page from a substantially rectangular exterior portion of the page along three sides of the page. The fourth side of the page forms the front of the visor. The exterior portion forms a continuous band that encircles the head. The interior portion is bisected by a fold line that approximately parallels the front of the visor.

1 Claim, 1 Drawing Sheet

PROGRAM SUN VISOR

FIELD OF THE INVENTION

This invention relates to a detachable program page constructed to form a sun visor.

BACKGROUND OF THE INVENTION

Those spectating at athletic events are frequently required to stare into the sun. Outdoor football games offer a prime example of the phenomenon. Programs are usually available at such sporting events. The publishers of the programs would be pleased to sell more programs. The advertisers in the programs would be pleased to receive heightened exposure. This invention claims a page of a sports program, which could be the back page, that detaches from the program and is constructed to form a trouble-free sun visor for one occasion. Wearing the visor can heighten the wearer's identification with the participants in the event and can heighten the exposure of an advertiser.

There are problems involved with designing a sun visor to be formed from a detachable page of program. The material that forms a program page, even the front or back cover page, does not naturally exhibit the desired rigidity and toughness. A trouble-free program sun visor, therefore, must be designed to overcome these problems presented by the material of a typical program page, that is a tendency to tear easily and not to retain shape.

U.S. Pat. No. 2,679,047 to Bozzi teaches a visor to be formed from a printed program for athletic events. The visor of Bozzi requires two pieces to be connected in order to form the band that encircles the head. Typically, pages of programs, however, do not have the requisite rigidity to form that connection reliably. They are likely to tear or come apart, even during one wearing. Such a troublesome visor is unsatisfactory and little better than no visor at all. An advertiser would not want to become associated with a visor that was not trouble-free. Bozzi's invention further requires the use of a full page spread, i.e., a double page from a printed program. The present invention is designed to be constructed from a single page of a standard athletic event program, which page could be the back page. The present invention offers a visor that cannot become separated without tearing and that offers no particularly weakened points susceptible of tearing.

Bozzi's invention further makes no use of the portion of the page that does not comprise either the band or the front of the visor. The present invention is adapted to offer this interior portion of the page as a particularly useful space for advertisement and team identification.

U.S. Pat. Nos. 4,246,659 to Lyons; 4,747,164 to Foulke; and 1,030,173 to Haggerty relate to hats or visors to be formed from a planar unitary blank of paper board. Part of the value of designing hats to be formed from a blank of paper board resides in the efficiency in manufacturing from an integral piece of material and the efficiency of shipping in a flat or knocked down condition. Such concerns do not relate to the present invention. Improving shipping and manufacturing efficiency for novelty hats is not related to providing a one-time sun visor for sporting events, constructed from materials on hand. Haggerty teaches a sun visor, eye shade and advertising device. Haggerty's advertising device, however, does not occupy the particularly prominent position of the front crown of the head, as it does in the present invention. Rather, Haggerty's advertising device drapes down the back of the neck. Further, since Haggerty, as with Lyons and Foulke, is not constrained to form his hat from a page of a program, Haggerty does not teach, and has no need to teach, a substantially rectangular interior portion. Lyons, like Haggerty, teaches a pop-up hat and blank for forming the same. Lyons, like Haggerty, is not constrained to form a hat from a detachable page of a program. Lyons does not teach a substantially rectangular interior portion. Foulke, as with the above, teaches a hat and method for making the hat that is not constrained to a blank formed of a detachable page of a program. Foulke does not teach a substantially rectangular interior portion. Neither Foulke, Haggerty or Lyons teach an interior portion bisected by a fold line substantially parallel to the front of the visor. The fold line of the present invention permits the interior portion to be strengthened by being doubled over. Such strengthening helps ensure that the advertising section maintains its shape. Lyons and Foulke are not concerned with advertising. Neither Lyons, Foulke or Haggerty are concerned with strengthening the interior section since they are working with a blank of paperboard that may be designed with the rigidity sufficient to serve the functions of the hat without any subsidiary support concerns.

U.S. Pat. No. 4,335,471 to Quigley teaches head gear formed of a resilient material such as foam rubber. Quigley's invention is not restrained to being formed from a detachable page of a program. Indeed, Quigley utilizes a foam material with substantial thickness to insure sufficient rigidity. Quigley's invention does not teach, and has no need for, the fold line bisecting the interior section.

It is an object of the present invention to teach the design of a page of a sports program that can be detached and used for a one-time trouble-free sun visor. The visor offers opportunity, by design and coloring, to identify the spectator with a participant of the sporting event and, possibly, to identify a supporting advertiser. Such a visor can be reversible wherein one side of the page displays the insignia of one team while the other side of the page displays the insignia of the other team. It is a further object of the invention for the visor to be trouble free. To that end, the visor is one-piece, utilizing the totality of the page and avoiding having to connect pieces of the program page paper together to form any part of the visor.

SUMMARY OF THE INVENTION

This invention comprises a sun visor to be constructed from a detachable page of a program. The page has a perforated line that separates a substantially rectangular interior portion of the page from a rectangular exterior band portion of the page along three sides of the page. The fourth side of the page forms the front of the visor. The exterior band portion forms a continuous, roughly rectangular band that encircles the head. The interior portion is bisected by a fold line that approximately parallels the front of the visor and is designed to be doubled over and turned up at the front of the head.

DETAILED DESCRIPTION OF THE PREFERRED EMBODIMENT

Figure 2:
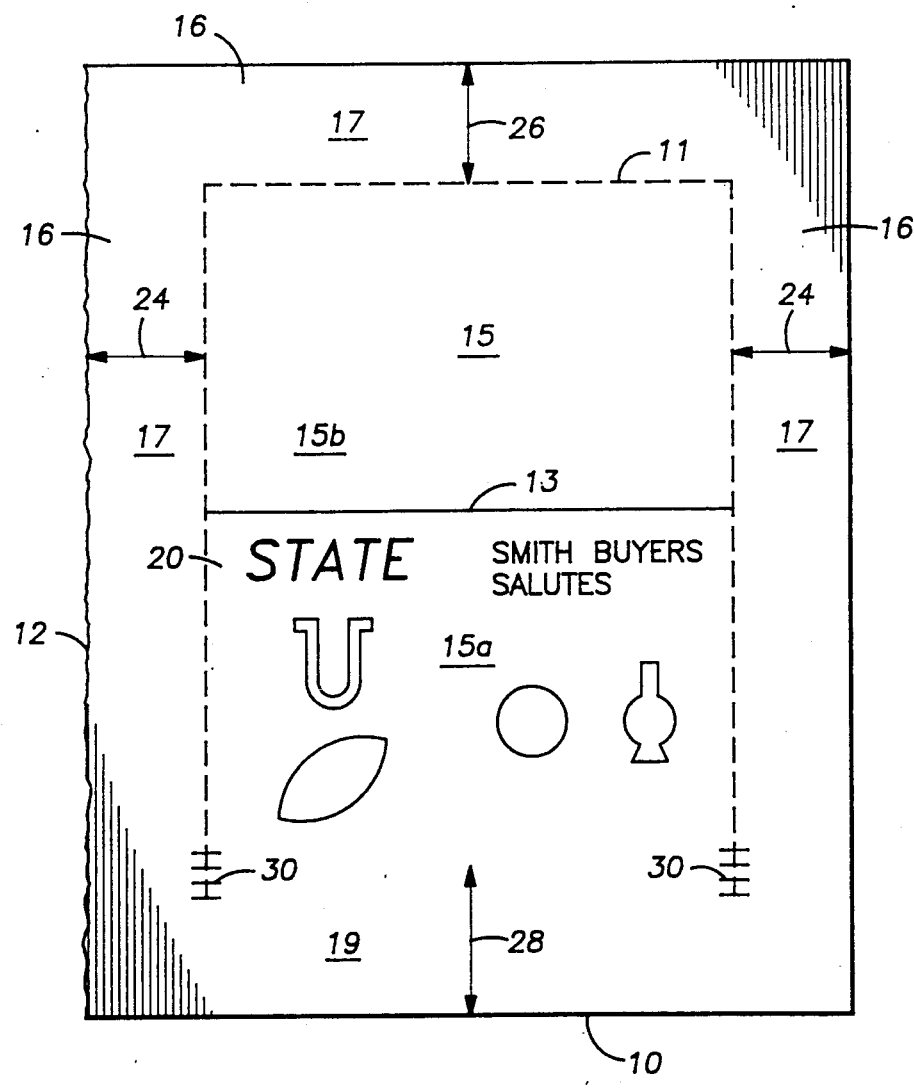
FIG. 2 is a top plan view of a detached page of a program showing the visor to be formed.

FIG. 2 illustrates the preferred embodiment for a detached page of a sporting event program that is constructed to form a one-time trouble-free sun visor. Edge 12 of the page is illustrated as having a somewhat ragged edge. The ragged edge indicates that this side of the page was torn or separated from the program. Dashed line 11 is a perforated line that separates a substantially rectangular interior portion 15 of the page from a substantially rectangular exterior band portion 17 of the page along three sides of the page. The front portion 19 of the page forms the front of the visor. When interior portion 15 is separated from exterior portion 17 by punching out along perforated line 11, exterior portion 17 forms a substantially rectangular band that will encircle the head. If the program measures 8½ by 11 inches, widths 24 and 26 in the preferred embodiment are approximately 1½ inches while width 28 is approximately 2½ inches. Width 28 may vary slightly as indicated by lines 30 drawn on the page across perforated line 11. Lines 30 indicate that the potential wearer may cease separating the interior portion from the exterior portion at several different points, thereby offering some variation in the size of the band to account for a variation in head sizes.

Interior portion 15 is subdivided into front interior portion 15a and rear interior portion 15b. The separation is delineated by fold line 13, printed clearly on the page. Either on the page or on a facing page, instructions as to how to form the visor should be printed, including the instruction to fold interior portion 15 along printed line 13. Interior portion 15a comprises a significant advertising space when the page is worn as a visor. Such space may identify the wearer with a team and/or the products of an advertiser. The page may be colored in the colors associated with one of the participants in the sporting event. The visor is reversible. The opposite side of the page may be colored and contain advertising material for another participant in the event. In this way, the wearer chooses which side to display as a means of asserting identity with one of the participants in the sporting event.

Figure 1:
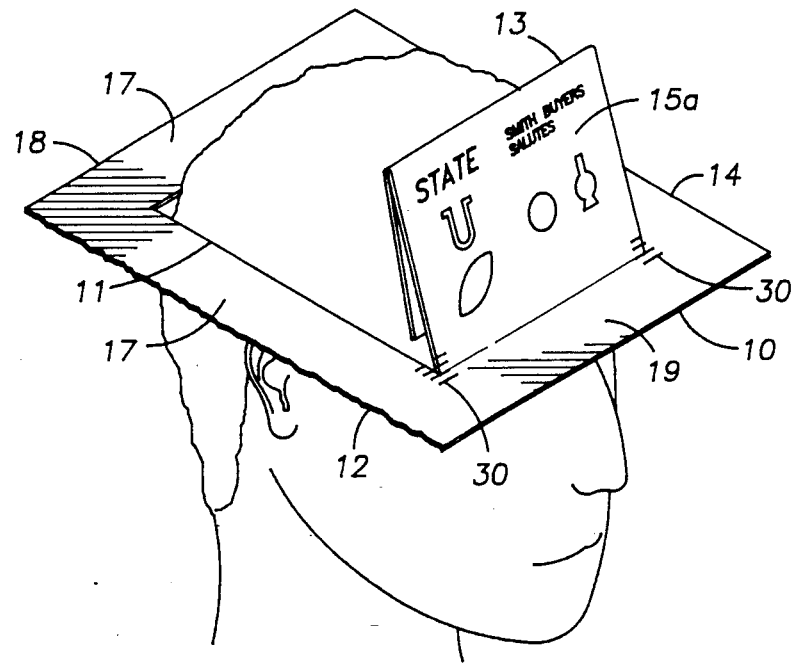
FIG. 1 is an elevation view of the visor of the present invention.

FIG. 1 illustrates the program page constructed into the visor and being worn.

Having described the invention above, various modifications of the techniques, procedures, material and equipment will be apparent to those in the art. It is intended that all such variations within the scope and spirit of the appended claims be embraced thereby.

What is claimed is:

1. A sun visor comprising a detachable program page having a perforated line that separates, along three sides of the page, a substantially rectangular interior portion of the page from a substantially rectangular exterior portion of the page such that the interior portion remains joined to the exterior portion along the fourth side of the page, the fourth side forming the front of the visor and the exterior portion forming a continuous, substantially rectangular band for encircling the head, and wherein the interior portion is bisected by a fold line that approximately parallels the front of the visor such that front and rear segments of the interior portion can be folded together and moved forward toward the front of the visor.

* * * * *